(12) United States Patent
Ceska et al.

(10) Patent No.: US 6,399,672 B1
(45) Date of Patent: Jun. 4, 2002

(54) OIL SOLUBLE METAL-CONTAINING COMPOUNDS, COMPOSITIONS AND METHODS

(75) Inventors: Gary W. Ceska, Exton; James P. Horgan, West Chester; Thomas W. Hazell, Exton; William R. Schaeffer, Glenmoore, all of PA (US)

(73) Assignee: Sartomer Technologies Co., Inc., Wilmington, DE (US)

(*) Notice: Subject to any disclaimer, the term of this patent is extended or adjusted under 35 U.S.C. 154(b) by 0 days.

(21) Appl. No.: 09/324,540

(22) Filed: Jun. 2, 1999

(51) Int. Cl.$^7$ .................................................. C08F 2/46
(52) U.S. Cl. ...................... 522/171; 522/171; 522/173; 522/178; 522/179; 522/181; 522/96; 522/180; 428/500; 428/513; 428/704
(58) Field of Search ................................ 522/173, 178, 522/179, 181, 182, 183, 96, 171, 80; 428/500, 513, 704

(56) References Cited

U.S. PATENT DOCUMENTS

| | | | |
|---|---|---|---|
| 3,689,427 A | * | 9/1972 | Hideaki et al. .......... 252/188.3 |
| 3,847,846 A | | 11/1974 | Asada |
| 3,899,382 A | | 8/1975 | Matsuda et al. |
| 4,165,877 A | | 8/1979 | Miller et al. |
| 4,264,075 A | | 4/1981 | Miller et al. |
| 4,495,326 A | | 1/1985 | Donatelli et al. |
| 4,500,466 A | | 2/1985 | Hayes et al. |
| 4,529,770 A | | 7/1985 | Hayes et al. |
| 4,715,607 A | | 12/1987 | Llort et al. |
| 4,716,409 A | | 12/1987 | Hart et al. |
| 4,720,526 A | | 1/1988 | Roland |
| 4,770,422 A | | 9/1988 | Isaac |
| 4,918,144 A | | 4/1990 | Fukuda |
| 5,126,501 A | | 6/1992 | Ellul |
| 5,202,450 A | | 4/1993 | Satake et al. |
| 5,208,294 A | | 5/1993 | Brown |
| 5,391,666 A | | 2/1995 | Satake et al. |
| 5,656,703 A | | 8/1997 | Costin et al. |
| 4,065,537 A | | 12/1997 | Miller et al. |
| 5,721,304 A | | 2/1998 | Pasqua, Jr. |
| 5,731,371 A | | 3/1998 | Nesbitt et al. |

FOREIGN PATENT DOCUMENTS

| | | | |
|---|---|---|---|
| EP | 0 648 822 A1 | * | 4/1995 |
| EP | 0 863 169 A2 | | 9/1998 |
| JP | 121902 | | 11/1926 |
| JP | 091572 | | 2/1977 |
| JP | 295285 | | 7/1991 |

OTHER PUBLICATIONS

Hideaki Matsuda and Takanori Okamoto, "Metal–Containing Cured Resins Based on Divalent Metal Salts of Ethylene Glycol–Methacrylate–Maleate," *Polymer Engineering and Science*, Jun., 1978, vol. 18, No. 8., pp. 628–633.

Hideaki Matsuda and Takanori Okamoto, "Preparation and Copolymerization of Divalent Metal Salts of Ethylene Glycol–Methacrylate–Phthalate," *Journal of Applied Polymer Science*, 1973, vol. 17, pp. 1941–1952.

T. Okamoto and H. Matsuda, "Effect of Divalent Metal Salts of Dibasic Acid Mono (Methacryloyloxypropyl) Esters on Adhesive Properties," *Int. J. Adhesion and Adhesives*, Jan., 1989, vol. 9, pp. 13–20.

* cited by examiner

Primary Examiner—James J. Seidleck
Assistant Examiner—Sanza McClendon
(74) *Attorney, Agent, or Firm*—Michael B. Fein; Cozen O'Connor

(57) ABSTRACT

Radiation curable compositions for coatings, adhesives, inks, and molded articles are disclosed. The radiation curable compositions comprise (A) at least one polymerizable, ethylenically unsaturated compound of one of the following formulas:

(I)

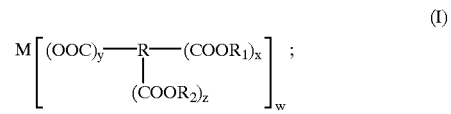

(II)

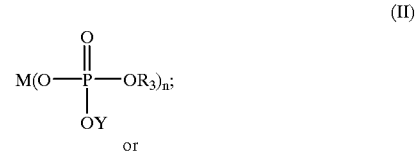

or (III)

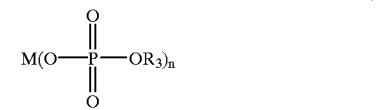

wherein

M is one or more metal atoms of valence n, wherein n=y·w, wherein M is optionally more than one metal atom, with the proviso that the global equivalent metal valence is n=w·y;

n is an integer of about 1–6;

R is a residue of a compound having anhydride and/or carboxylic acid groups with initial equivalent carboxy equivalent functionality defined by the equation f=x+y+z, wherein f is an integer of about 2 to 30;

$R_1$ is a residue of a hydroxy-containing ethylenically unsaturated compound;

$R_2$ is H or a residue of a hydroxy containing ethylenically unsaturated compound different from $R_1$;

$R_3$ is a residue of a hydroxy-containing ethylenically unsaturated compound;

w is the number of moieties having residue R required for valence n;

x is an integer of about 1 to f–1;

y is an integer of about 1 to 2 (the number of intramolecular carboxylates bonded to M);

z is an integer of about 0 to f–2;

Y is H or $R_3$; and (B) at least one copolymerizable ethylenically unsaturated monomer or oligomer.

37 Claims, No Drawings

OIL SOLUBLE METAL-CONTAINING COMPOUNDS, COMPOSITIONS AND METHODS

BACKGROUND

1. Field of the Invention

This invention relates to radiation curable coatings, adhesives, inks, and molded articles. The invention also relates to clear, transparent molded articles useful as lenses, laminating resins, and novel unsaturated metal sulfates.

2. Description of the Prior Art

The use of metal (meth)acrylates such as zinc, calcium, and magnesium salts of acrylic or methacrylic acids as crosslinking monomers for use with elastomers to promote adhesion to substrates is well known. As described in Proudfit, U.S. Pat. No. 5,314,187, for example, zinc acrylate, zinc diacrylate, and zinc methacrylate are particularly suitable crosslinking agents for elastomers such as EPDM, 1,4-butadiene, isoprene, chloroprene, and the like. Ahmad et al., U.S. Pat. No. 5,506,308, teaches use of unsaturated carboxylic metal salts such as zinc diacrylate in curable elastomeric compositions wherein the elastomer may be a nitrile rubber, EPDM, EVA, and the like. Other prior patents which teach zinc acrylate, zinc diacrylate, zinc methacrylate, calcium diacrylate, and calcium dimethacrylate as crosslinking agents for elastomers include U.S. Pat. Nos. 5,731,371; 5,721,304; 5,656,703; 5,208,294; 5,126,501; 4,918,144; 4,770,422; 4,720,526; 4,715,607; 4,716,409; 4,529,770; 4,500,466; 4,495,326; 4,165,877; 4,065,537; and 4,264,075.

One disadvantage of such metal salts of carboxylic acids is their poor oil solubility. For example, they are relatively insoluble in organic monomers and oligomers.

Soluble zinc and calcium salts of ethylene glycol-methacrylate-phthalate (EMD) prepared in aqueous solution, and then copolymerized with methyl methacrylates (MMA), styrene (ST), and hydroxyethyl methacrylate (HEMA) were disclosed by Matsuda, et al., Preparation and Copolymerization of Divalent Metal Salts of Ethylene Glycol-Methacrylate-Phythalate, *J. App. Poly. Sci.*, 17, 1941–1952 (1973), as ionic crosslinkers. The resultant crosslinked copolymers are shown to have improved physical properties.

U.S. Pat. No. 3,847,846 assigned to Kansai Paint Co., Ltd., teaches electrically conductive resins prepared from metal salts of certain sulphonates, phosphates, or phosphoric acid diesters, with an epoxide, optional solvent, polymerization initiator, and/or photosensitizer, and useful for magnetic tape and the like.

Matsuda, et al., U.S. Pat. No. 3,899,382, teaches polyvalent metal salts of compounds such as diethylene glycol methacrylate phthalate, mixed with an organic peroxide.

Matsuda, et al., Metal-Containing Cured Resins Based on Divalent Metal Salts of Ethylene Glycol-Methacrylate-Maleate, *Poly Eng. and Sci.*, 18, No. 8, 628–633, June 1978, teach solubility of such salts in St., MMA, and EA, and copolymerization with such vinyl monomers to produce polymers having high heat distortion temperature, tensile strength, compressive strength, impact strength, and Rockwell hardness, as well as resistance to chemical attack.

Japanese Kokai 295285 of May 7, 1991, teaches use of magnesium, aluminum, or calcium salts of unsaturated phosphate compounds as additives for coatings to improve adhesion to metals.

Okamoto, et al., Effect of divalent metal salts of dibasic acid mono (methacryloyloxy propyl) esters on adhesive properties, *Int. J. Adhesion and Adhesives*, 9, No. 1, January 1989, teach peroxide cured adhesives prepared by copolymerizing such monomers with hydroxy propyl methacrylate (HPM).

The art of radiation curable coatings, adhesives, and inks is different from the art of peroxide curable polymers. In the radiation curable field, the current art uses only oil insoluble metal salts as adhesion promoters. No one has previously proposed oil soluble metal salts of carboxylic acids in the radiation curable art.

3. Objects

It is, therefore, an object of the present invention to provide improved radiation curable adhesives, coatings, and inks, transparent molded articles useful as lenses, and thermoset laminating resins.

It is another object to provide novel polymerizable, unsaturated metal sulfates which are oil soluble and useful in such compositions.

SUMMARY OF THE INVENTION

These objects, and others which will become apparent from the following disclosure, are provided by the invention which, in one aspect, includes a composition suitable for a radiation cured coating, adhesive, ink, or photoresist comprising (A) at least one polymerizable, ethylenically unsaturated compound of the formula

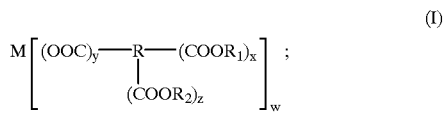

(I)

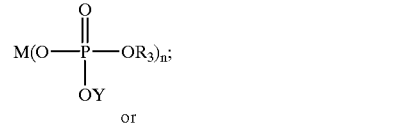

(II)

or

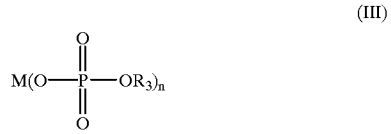

(III)

wherein

M is one or more metal atoms of valence n, wherein n=y·w, and wherein M is optionally more than one metal atom, with the proviso that the global equivalent metal valence is n=w·y;

n is an integer of about 1–6;

R is a residue of a compound having anhydride and/or carboxylic acid groups with an initial equivalent carboxy equivalent functionality defined by the equation f=x+y+z, wherein f is an integer of about 2 to 30;

$R_1$ is a residue of a hydroxy-containing ethylenically unsaturated compound;

$R_2$ is H or a residue of a hydroxy containing ethylenically unsaturated compound different from $R_1$;

$R_3$ is a residue of a hydroxy-containing ethylenically unsaturated compound;

w is the number of moieties having residue R required for metal valence n;

x is an integer of about 1 to f−1;

y is an integer of about 1 to 2 (the number of intramolecular carboxylates bonded to M);

z is an integer of about 0 to f–2;

Y is H or $R_3$; and (B) at least one copolymerizable ethylenically unsaturated monomer or oligomer.

In another aspect, the invention includes a polymer, especially in the form of a coating, adhesive, ink, or molded article prepared by curing such a composition in the presence of a free radical initiator and/or radiation.

A further aspect of the invention is a solution of compound (A) in copolymerizable ethylenically unsaturated monomer or oligomer (B), alone or in an inert solvent. Such solutions can be prepared by forming compound (A) in the presence of the copolymerizable ethylenically unsaturated monomer or oligomer (B) and optionally in the presence of an inert solvent.

Still another aspect of the invention is a molded article polymerized from such a composition, the article having a refractive index useful for lenses.

A still further aspect is a process of preparing polymerizable, ethylenically unsaturated compounds (A) of formula (I), (II), (III) comprising reacting a hydroxy compound with a polyacid, anhydride, sulfur oxide, or phosphorus oxide compound to form an acid functional compound, and reacting the acid functional compound with a metal compound.

In another aspect, the invention includes a thermoset copolymer of a monomer mixture comprising (A) a compound according to formula (I), (II), or (III), and a (B) a polyfunctional (meth)acrylate or allylic compound.

Another aspect is a composition suitable for laminating resins having high heat distortion temperature, comprising an ethylenically unsaturated monomer, a free radical initiator, and a crosslinking monomer according to formula (I), (II), or (III).

The invention also comprises a compound of formula (III), i.e., a polymerizable, ethylenically unsaturated sulfate compound of the formula

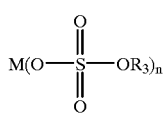

(III)

wherein

M=metal;

n=valence of M; and $R_3$=a residue of an unsaturated hydroxy compound; the compound being useful in making certain of the radiation curable compositions.

DETAILED DESCRIPTION OF THE INVENTION

The oil soluble metal salts of formula (I), (II), or (III) useful in the radiation curable compositions of the invention can be prepared by any appropriate process. A preferred process comprises reacting a hydroxy compound with a carboxylic polyacid or anhydride, a sulfur oxide compound, or a phosphorus oxide compound to form an acid functional compound, and reacting that acid functional compound with a metal compound. The compounds of formula (I) are prepared, from carboxylic polyacids or anhydrides, whereas the compounds of formula (II) are prepared from phosphoric acids, and the compounds of formula (II) are prepared from sulfuric acids.

The hydroxy compounds used in such preparation can be saturated or unsaturated compounds. Saturated hydroxy compounds can be used to prepare compounds of formula (I) when the polyacid and/or anhydride compound contains ethylenic unsaturation which can be employed in the resultant compound for polymerization, especially with other polymerizable, ethylenically unsaturated compounds.

For the hydroxy compounds containing an ethylenically unsaturated group, the unsaturation can be provided by (meth)acrylic, allyl, propenyl, and/or vinyl groups. As used herein, the term "(meth)acrylic" is intended to include methacrylic, acrylic, and mixtures thereof.

Some examples of such suitable hydroxy compounds include hydroxyethyl (meth)acrylate, hydroxypropyl (meth)acrylate, hydroxybutyl (meth)acrylate, ($C_1$ to $C_6$) alkyl glycidyl (meth)acrylates, aryl glycidyl (meth)acrylates, allyl glycidyl (meth)acrylate, trimethylolpropane mono- and di-(meth)acrylate, pentaerythritol mono-, di-, and tri-(meth)acrylate, dipentaerythritol mono-, di-, tri-, tetra-, and penta-(meth)acrylate, glycerol mono- and di-(meth)acrylate, neopentyl glycol mono(meth)acrylate, hexanediol mono (meth)acrylate, tris(2-hydroxyethyl)isocyanurate mono- and di-(meth)acrylate, ethoxylated or propoxylated versions of all of the above, polyethylene glycol mono(meth)acrylate, polypropylene glycol mono(meth)acrylate, polyethylene/propylene glycol mono(meth)acrylate, polybutylene glycol mono(meth)acrylate, polytetramethylene glycol mono (meth)acrylate, hydroxy polycaprolactone mono(meth) acrylate, and the like. Residues of these compounds are represented by $R_1$ or $R_3$ in formulas (I), (II), and (III).

Examples of hydroxy-allyl compounds include allyl alcohol, propoxylated or ethoxylated allyl alcohol, cinnamyl alcohol, crotyl alcohol, 3-butene-1-ol, 3-butene-2-ol, linalool, 2-cyclohexen-1-ol, 2-cyclopenten-1-ol, 2-butene-1,4-diol, glycerol mono- and di-allyl ethers, trimethylolpropane mono- and di-allyl ethers, and the like.

Hydroxy-propargyl compounds, for example, propargyl alcohol, propoxylated or ethoxylated propargyl alcohol, 2-butyn-1-ol, 3-butyn-1-ol, 3-butyn-2-ol, and the like are also suitable.

Other hydroxy compounds such as hydroxy-vinyl compounds, for example, ethylene glycol vinyl ether, propylene glycol vinyl ether, 1,4-butanediol vinyl ether, 1,3-butanediol vinyl ether, 1,6-hexanediol vinyl ether, 2-methyl-1,3-propane diol vinyl ether, di(ethylene glycol) vinyl ether, di(propylene glycol) vinyl ether, and the like can be used.

In the case of compounds of formula (I), polyacids or anhydrides which can be reacted with hydroxy compounds have either two or more carboxylic acid groups, or at least one anhydride group, or a combination thereof, such as one anhydride group and one carboxyl group. The hydroxy compound reacts with this compound to form a carboxyl functional compound which is suitable for reaction with a metal compound to form an oil soluble, polymerizable salt. The carboxy equivalent functionality of polycarboxylic acids and anhydrides is about 2–30. Preferably, the range is about 2–6.

For the compounds of formula (I), some suitable compounds containing anhydride and/or carboxyl groups which react with the hydroxyl compounds include phthalic anhydride, isophthalic acid, terephthalic acid, tetrabromophthalic anhydride, tetrahydrophthalic anhydride, hexahydrophthalic anhydride, itaconic anhydride, itaconic acid, phthalic acid, trimellitic anhydride (which contains one anhydride and one carboxyl group), pyromellitic anhydride, 5-norbornene-endo-2,3-dicarboxylic anhydride, naphthyl anhydride, naphthalene tetracarboxylic acid dianhydride, maleic anhydride, succinic anhydride, chlorendic anhydride, maleic acid, succinic acid, fumaric acid, oxalic acid, malonic acid, glutaric acid, adipic acid, dimer fatty acids, styrene/maleic anhydride polymers, and (meth)acrylic acid polymers and co-polymers.

In the case of compounds of formula (II), phosphorous containing compounds such as phosphorous pentoxide are used in place of the carboxylic anhydride compounds, and reacted with the unsaturated hydroxy compounds to form phosphate esters having acid functionality suitable for reaction with the metal salt.

In the case of compounds of formula (III), sulfur containing compounds such as sulfur trioxide are reacted with the unsaturated hydroxy compound to form sulfate esters which have acid functionality and later react with the metal compound. The compounds of formula (III) are novel.

Suitable metal compounds are those which can provide one or more metal (M) ions when reacted with the half esters prepared as described above. The suitable metals include lithium, sodium, potassium, cesium, magnesium, calcium, strontium, barium, titanium, zirconium, vanadium, chromium, molybdenum, tungsten, manganese, iron, cobalt, nickel, palladium, copper, zinc, cadmium, mercury, boron, aluminum, gallium, indium, silicon, germanium, tin, lead, antimony, bismuth, and the like. The metal compound can be, for example, the oxide, halide, alkoxide, hydroxide, nitrate, sulfate, carboxylate, and carbonate. The most preferred metal compound is zinc oxide since it reacts very easily, and is readily available.

The compounds of formulas (I), (II), and (III) can be prepared in an inert solvent, with very simple reaction conditions. For example, no catalyst is required. Water generated during the preparation can be removed by azeotropic distillation.

Suitable inert solvents include ethyl acetate, toluene, benzene, xylenes, hexane, heptane, and the like.

After preparation, the polymerizable unsaturated compounds are dissolved in an organic compound which is preferably also unsaturated, and is preferably copolymerizable with the compounds of formulas (I), (II), or (III). Some of such compounds are known in the art as reactive diluents.

The reactive diluents can be monomers or oligomers. Suitable reactive diluents include (meth)acrylic monomer, (meth)acrylic oligomer, vinyl monomer, vinyl oligomer, allyl monomer, allyl oligomer, propenyl monomer, propenyl oligomer, glycidyl ether, glycidyl ester, and the like.

Suitable (meth)acrylic monomers and oligomers include (meth)acrylate esters of $C_1$–$C_{20}$ alcohols, (meth)acrylate esters of ethoxylated or propoxylated $C_1$–$C_{20}$ alcohols, di(meth)acrylate esters of $C_2$–$C_8$ diols, di(meth)acrylate esters of ethoxylated or propoxylated $C_2$–$C_8$ diols, polyethylene glycol di(meth)acrylates, polypropylene glycol di(meth)acrylates, polyethylene/propylene glycol di(meth)acrylates, trimethyolpropane tri(meth)acrylate, ethoxylated or propoxylated trimethyolpropane tri(meth)acrylate, pentaerythritol tetra(meth)acrylate, ethoxylated or propoxylated pentaerythritol tetra(meth)acrylate, ethoxylated or propoxylated bisphenol-A di(meth)acrylate, bisphenol-A glycerolate di(meth)acrylate, $C_1$–$C_{20}$ alkyl glycidyl (meth)acrylates, aryl glycidyl (meth)acrylates, glycidyl (meth)acrylate, and the like.

Suitable vinyl monomers and oligomers include styrene, α-methylstyrene, vinyl toluene, bromostyrenes, tert-butylstyrene, N-vinylpyrrolidone, N-vinylcaprolactam, N-vinylformamide, vinyl acetate, vinyl propionate, vinyl pivalate, vinyl stearate, vinyl 2-ethylhexanoate, methyl vinyl ketone, ethyl vinyl ketone, vinyl ethers of $C_1$–$C_{20}$ alcohols, 2,3-dihydrofuran, vinyl(meth)acrylate, allyl vinyl ether, and divinyl ether of $C_1$–$C_{20}$ diols, for example.

Suitable propargyl monomers and oligomers include dipropargyl ether, propargyl ethers of $C_1$–$C_{20}$ alcohols, propargyl (meth)acrylate, and the like.

After the reactive diluent is combined with the compound of formula (I), (II), and/or (III), the resultant solution can be stored without reacting, if desired, and then used to prepare the coatings, adhesives, and inks by conventional radiation cure techniques, for example, ultraviolet light (UV), or election beam radiation (EB), or microwave.

When the radiation is provided by UV, the composition should also include a photoinitiator. Such a photoinitiator is not necessary when EB is the source of radiation. Suitable photoinitiators for radiation curable compositions comprising a compound of formula (I), (II), or (III) and an ethylenically unsaturated comonomer or oligomer are those which promote free radical polymerization, generally of the unimolecular or bimolecular type. Examples of unimolecular type include isobutyl benzoin ether, benzil dimethoxy ketone, hydroxy aceto-phenone, acylphosphine oxide, and amino-alkylphenones. Examples of bimolecular type include benzophenone, derivatives of benzophenone, and combinations thereof with a hydrogen donating source.

For certain applications, it is not necessary or desirable to blend the compounds of formulas (I),(II), or (III) with reactive diluents. For other applications an inert solvent can be included in the compositions. In some cases, the compounds of formulas (I), (II), or (III) can be prepared in inert solvent and/or in the presence of copolymerizable ethylenically unsaturated monomer.

Hybrid cure polymerization of compositions comprising oil soluble polymerizable metal salts of formulas (I), (II), or (III), ethylenically unsaturated reactive diluent, and either epoxy resins or isocyanates can be carried out using a dual cure polymerization initiation system. In hybrid or dual cure systems, free radical polymerization of the polymerizable, metal salt with reactive diluent occurs simultaneously with, but independently of, a second type of polymerization, for example, a cationic initiated epoxy polymerization. Those skilled in the art will recognize other suitable polymerization reactions.

Cationic photoinitiators may also be used in the invention. Such cationic photoinitiators include diaryl ammonium salts and triaryl sulfonium salts. Examples of the cationic photoinitiators include diaryliodonium hexafluoroantimonate, triarylsulfonium hexafluoroantimonate, triarylsulfonium hexafluorophosphate, cyclopentadiene hexafluorophosphate, and the like.

Prior art formulations which employ oil insoluble metal salt crosslinking agents such as zinc diacrylate and zinc dimethacrylate can be modified and improved according to this invention by replacing the oil insoluble agents with a compound of formula (I), (II), and/or (III), with resultant great and surprising improvements in properties in many applications. The oil soluble metal salts can be used in combination with conventional insoluble metal salts such as zinc diacrylate.

Since the use of the insoluble salts in coatings or adhesives causes reduced gloss, whereas the compounds of the invention do not reduce gloss, combinations can be used to achieve controlled gloss. Use of the oil soluble metal salt compounds causes improved adhesion of the adhesives or coatings to substrates, improved abrasion resistance, heat resistance, clarity, tensile strength, modulus, interfacial adhesion, and toughness. Among the applications for which the coatings and adhesives are useful are can coatings, flooring coatings, pipe coatings, inks which have improved heat resistance, photoresists, coating metals where antimicrobial properties are desired, marine coatings, powder coatings, and the like. With powder coatings, the composition is solid at room temperature.

In the case of molded articles polymerized from solutions of the invention, very clear products can be obtained, with refractive index and transparency substantially matching that of glass, making the moldings useful for many applications, for example, lenses. In the case of lenses, the preferred refractive index is about 1.50 to 1.60. The preferred copolymerizable monomer is diallyl glycol carbonate.

Clear, transparent molded articles can be thermoset copolymers of a polyfunctional (meth)acrylate or allylic compound and a metal salt of formula (I), (II), (III), and can further include other monomers, for example, monofunctional (meth)acrylates, styrene, vinyl ethers, epoxys, and propenyl ethers.

The invention also encompasses compositions suitable as laminating resins. The laminating resins of the invention have a high heat distortion temperature. The laminating resin compositions of the invention include at least one compound of formula (I),(II), and/or (III) and at least one laminating resin. As used herein, "laminating resins" are unsaturated polyester resins based on maleic anhydride. These are made from maleic anhydride, glycols (such as propylene glycol, ethylene glycol, diethylene glycol, and the like), and dicarboxylic acids (such as adipic acid, orthophthalic acid, isophthalic acid, and the like).

The invention includes a process for coating a substrate with the composition. Suitable substrates may be of any type. A preferred substrate is metal. In the process, a substrate is coated with a composition comprising at least one compound of the formula (I), (II), or (III), and at least one ethylenically unsaturated monomer or oligomer, and is subsequently irradiated. The process may also include exposing the coating composition to heat. The cured coating compositions are able to withstand pasteurization and retort conditions substantially without degradation of the cured coating.

Coating compositions may also be formed of at least one compound of the formula (I), (II), or (III), and a fatty acid-modified alkyd resin. The amount of the compound of formula (I), (II), or (III) should be sufficient to improve the adhesion of the coating to the substrate to be coated. In curing the coating composition containing the fatty acid-modified resin, a free radical initiator may be added along with a metal salt drying agent in an amount effective to aid in the decomposition of the free radical initiator. The invention also embraces the method of coating a substrate with the coating composition containing the fatty acid-modified alkyd resin and curing the coating composition.

The fatty acid-modified alkyd resins suitable for use in the invention include polyester resins based on polyhydroxy compounds with carboxylic anhydride and a fatty acid. These compounds may be used with free radical initiators such as organic peroxides. Examples of suitable organic peroxides include cumene hydroperoxide, methylethyl ketone peroxide, and the like.

The metal salt drying agents which may be used in this embodiment of the invention include a cobalt naphthanate, cobalt octoate, and the like.

Various additives which are well known may be incorporated in the polymerizable solutions. Although the oil insoluble polymerizable metal salts of the prior art should not be incorporated for most applications of the invention, they may be added to obtain certain effects, for example when low gloss is desired.

The following non-limiting examples illustrate a few embodiments of the invention.

EXAMPLES

In the following examples, all parts and percentages are by weight, unless otherwise indicated.

Example 1

Preparation of Zinc Salt of Phthalic Anhydride-Hydroxyethyl Methacrylate Half Ester A 2 L 4-neck round bottom flask equipped with a mechanical stirrer, air sparge, temperature control, Dean-Stark trap, and condenser was charged with phthalic anhydride (609 gm, Aldrich, 99%), methyl hydroquinone (1.2 gm) and hydroxyethyl methacrylate (589 gm, Rocryl 400). The mixture was heated to 70° C. for 1 hr, to 95° C. for 1 hr, and then to 110° C. for 7 hrs. The product half-acid ester (1196 gm) had an acid value of 205 mg KOH/gm, APHA color of 184, and was clear.

A 1 L 4-neck flask equipped as above was charged with ZnO (50.46 gm, Aldrich), toluene (402 gm), and methylhydroquinone (0.24 gm). Agitation was started and the half-acid ester from above (401.6 gm) was added over 10 minutes. The mixture was heated to reflux for 1.5 hrs and the water generated was removed by azeotropic reflux. The mixture was cooled to ambient temperature and filtered to remove a small amount of solids. The solvent was removed at ca. 94°0C. and 20 mm Hg pressure to give the product zinc salt (398 gm) of the invention as a viscous oil.

The product when dissolved in 35 wt % trimethylolpropane triacrylate formed a solution of the invention which was slightly hazy with an APHA color of 52, Brookfield viscosity (25 ° C. , #27 spindle, 1 rpm) of 118,000 cPs, and RI (25° C.) of 1.5126.

Example 2

Zinc Salt of Phthalic Anhydride-Hydroxyethyl Acrylate Half Acid Ester

A 1L 4-neck flask equipped as in Example 1 was charged with phthalic anhydride (268.2 gm), methyl hydroquinone (0.50 gm) and hydroxyethyl acrylate (231.3 gm, Rocryl 420). The mixture was heated to 110° C. for 6.5 hrs to give a product half-acid ester (496.4 gm) with an acid value of 211 mg KOH/gm.

A 1 L flask equipped as in Example 1 was charged with toluene (240 gm), heptane (60 gm) and zinc oxide (48.7 gm). Agitation was started and the half-acid ester (350 gm) was added over 45 minutes. The reaction mixture was heated to reflux for 2 hrs and the water generated was removed by azeotropic reflux. The mixture was cooled to ambient temperature, acetone (200 gm) was added and the mixture filtered to remove a small amount of solids. The solvent was removed at ca. 94° C. and 20 mm Hg pressure to give the product zinc salt (298 gm) as a viscous oil.

The product when dissolved in 52 wt % tripropylene glycol diacrylate had APHA color of 80, Brookfield viscosity (25° C., #27 spindle, 20 rpm)=7680 cPs, and RI (25° C.) of 1.4916.

Example 3

Zinc Salt of Succinic Anhydride-Dodecyl Glycidyl Acrylate Half Acid Ester

A 1 L flask equipped as in Example 1 was charged with dodecyl glycidyl acrylate (the 1:1 addition product of dodecyl glycidyl ether and acrylic acid) (439.4 gm) and succinic anhydride (127.1 gm) and the mixture was heated 110° C. for 6 hrs. The mixture was cooled to ambient temperature and filtered to remove a small amount of solids. The product half-acid ester (552 gm) was obtained as a liquid with an acid value of 123 mg KOH/gm.

A 1 L flask equipped as in Example 1 was charged with toluene (150 gm), heptane (37 gm), the half-acid ester (401 gm), methyl hydroquinone (0.44 gm ) and zinc oxide (36.1 gm). The reaction mixture was heated to reflux for 2 hrs and the water generated was removed by azeotropic reflux. The mixture was cooled to ambient temperature, toluene (323 gm) was added and the mixture filtered to remove a small amount of solids. The solvent was removed at ca. 74 to 94° C. and 150 to 35 mm Hg pressure to give the product zinc salt (348 gm) as a viscous oil.

The product had Gardner color of 7.8, Brookfield viscosity (25 ° C. , #27 spindle, 10 rpm) of 16,000 cPs and RI (25° C.) of 1.4691.

Example 4

Zinc Salt of Half Acid Ester of Phenyl Glycidyl Acrylate and Phthalic Anhydride

Step 1. A 1 L flask equipped as in Example 1 was charged with phenyl glycidyl acrylate (the 1:1 addition product of phenyl glycidyl ether and acrylic acid) (373.6 gm) and phthalic anhydride (226.4 gm) and the mixture was heated 110° C. for 7 hrs to give a product half-acid ester (607.6 gm) with an acid value of 154 mg KOH/gm.

Step 2. A 2 L flask equipped as above was charged with toluene (320 gm), heptane (80 gm), the half-acid ester from Step 1 (895 gm), and zinc oxide (81.4 gm). The reaction mixture was heated to reflux for 7 hrs and the water generated was removed by azeotropic reflux. The mixture was cooled to ambient temperature, toluene (700 gm) was added and the mixture filtered to remove a small amount of solids. The solvent was removed at ca. 95 ° C. and 20 mm Hg pressure to give the product zinc salt (850 gm) as a viscous oil.

The product, when dissolved in 32 wt % phenyl glycidyl acrylate, had APHA color of 158 and Brookfield viscosity (25° C., #27 spindle, 2 rpm) of 100,000 cPs.

Example 5

Zinc Salt of Half Acid Ester of Caprolactone Acrylate and Phthalic Anhydride

A 1 L flask equipped as in Example 1 was charged with caprolactone acrylate (the ring-opening product of two moles of caprolactone by one mole of hydroxy ethyl acrylate) (378.8 gm) and phthalic anhydride (148.1 gm) and the mixture was heated 110° C. for 6 hrs to give a product half-acid ester (523 gm) with an acid value of 116 mg KOH/gm.

A 1 L flask equipped as above was charged with toluene (148 gm), heptane (37 gm), the half-acid ester from Step 1 (400 gm), methyl hydroquinone (0.44 gm) and zinc oxide (30.6 gm). The reaction mixture was heated to reflux for 3 hrs and the water generated was removed by azeotropic reflux. The mixture was cooled to ambient temperature, toluene (346 gm) was added and the mixture filtered to remove a small amount of solids. The solvent was removed at ca. 95 C. and 20 mm Hg pressure to give the product zinc salt (382 gm) as a viscous oil.

The product had APHA color of 77, Brookfield viscosity (25° C., #27 spindle, 2 rpm) of 92,700 cPs and RI (25° C.) of 1.5087.

Example 6

Zinc Salt of Half Acid Ester of Maleic Anhydride and Ethoxylated Allyl Alcohol

A 1 L flask equipped as in Example 1 was charged with ethoxylated allyl alcohol (5 moles of EO) (630 gm), maleic anhydride (201.8 gm)methyl hydroquinone (0.21 gm) and BHT (0.83 gm) and the mixture was heated 110° C. for 8 hrs to give a product half-acid ester (827 gm) with an acid value of 140 mg KOH/gm.

A 2 L flask equipped as in Example 1 was charged with toluene (273 gm), heptane (68 gm), the half-acid ester from Step 1 (728 gm) and zinc oxide (67.1 gm). The reaction mixture was heated to reflux for 2 hrs and the water generated was removed by azeotropic reflux. The mixture was cooled to ambient temperature, toluene (400 gm) and heptane (100 gm) were added and the mixture filtered to remove a small amount of solids. The solvent was removed at ca. 95 ° C. and 20 mm Hg pressure to give the product zinc salt (700 gm) as a viscous oil.

The product had Gardner color of 3.3 and Brookfield viscosity (250 C, #27 spindle, 20 rpm) of 5020 cPs.

Example 7

Zinc Salt of Phosphorous Pentoxide-Hydroxyethyl Methacrylate Ester

A 1 L flask equipped as in Example 1 was charged with toluene (118 gm), heptane (29 gm), and zinc oxide (55.2 gm). Agitation was started and a 50% solution (532.7 gm) of hydroxy ethyl methacrylate phosphate ester in ethoxylated trimethylolpropane triacrylate was added over 5 minutes. The reaction mixture was heated to reflux for 30 minutes and the water generated was removed by azeotropic reflux. The mixture was cooled to ambient temperature and filtered to remove a small amount of solids. The solvent was removed at ca. 95° C. and 20 mm Hg pressure to give a solution of the product zinc salt in ethoxylated trimethylolpropane triacrylate (514.5 gm).

The product solution had Gardner color of 4.1 and Brookfield viscosity (25 ° C. #27 spindle, 20 rpm) of 8710 cPs.

Example 8

Solubility of Zn Salts in Organic Compounds

Each of the polymerizable, ethylenically unsaturated compounds prepared in Examples 1–7 was mixed with various organic compounds to determine solubility, and compared with the corresponding zinc dimethacrylate and zinc diacrylate to determine solubility. In each case, the compound of the invention was completely soluble, whereas the zinc dimethacrylate and zinc diacrylate salts of the prior art were insoluble. The organic compounds tested with the products of each of the preceding examples were as follows:
Example 1:
  Diethylene glycol dimethacrylate
  Polypropylene glycol monomethacrylate
Example 2:
  1,3-Butylene Glycol Diacrylate
  1,4-Butanediol Dimethacrylate
  1,6-Hexanediol Diacrylate
  Tripropylene Glycol Diacrylate
  Trimethylolpropane Triacrylate
  Propoxylated Neopentyl Glycol Diacrylate
Example 3:
  Isodecyl Acrylate
  Trimethylolpropane Triacrylate Propoxylated Neopentyl Glycol Diacrylate
1,3-Butylene Glycol Diacrylate
Polyethylene Glycol(200) Diacrylate Example 4:
  1,3-Butylene Glycol Diacrylate
  Tripropylene Glycol Diacrylate
  Trimethylolpropane Triacrylate
  Phenyl Glycidyl Acrylate Example 5:
  1,3-Butylene Glycol Diacrylate
  1,6-Hexanediol Diacrylate
  Trimethylolpropane Triacrylate
  Propoxylated Neopentyl Glycol Diacrylate
  Dodecyl Glycidyl Acrylate Example 6:
  Trimethylolpropane Triacrylate
  Propoxylated Neopentyl Glycol Diacrylate Example 7:
  Ethoxylated Trimethylolpropane Triacrylate.

In each case, the metal salts of the invention were soluble in each of the solvents.

Example 9

UV Curable Coating Compositions

In this example, the following materials are represented by the following abbreviations:
A—bisphenol-A epoxy diacrylate
B—aliphatic urethane (acrylated isophorone diisocyanate/polyester polyol urethane) in 20% trimethylolpropane glycidyl ether diacrylate
C—zinc diacrylate (prior art)
D—organic soluble zinc salt of Example 1 dissolved in 50% 1, 3-butylene glycol diacrylate
E—1,3-butylene glycol diacrylate
F—dipropylene glycol diacrylate
G—ethoxylated trimethylolpropane triacrylate
H—alpha hydroxy ketone Zinc Diacrylate (ZDA) is a metallic based fine white solid powder that is difunctional in nature. It is typically used in peroxide, amine or ultraviolet light induced curable coatings to enhance adhesion to metal, plastic and wood substrates. Since ZDA is a fine white solid powder it may also be used as a gloss reducing agent for, but not limited to, coatings furniture or vinyl or wood flooring, The gloss reducing effect of the solid ZDA was tested in two typical wood topcoat formulations. One was based on an Epoxy Acrylate oligomer while the other employs a Urethane Acrylate oligomer. In addition to measuring the effects on gloss, the chemical resistance, flexibility, adhesion, abrasion resistance and hardness was tested on aluminum and wood substrate.

Coating compositions according to the invention were prepared and compared to corresponding coating compositions of the prior art by applying the compositions to either a wood composite having a paper laminate or to aluminum Q panels (Q-46) using a number 4 wire wound rod to yield a film thickness of about 12 microns, followed by curing using two 300 watts per inch mercury lamps at a line speed of 20 feet per minute. The resultant coated wood and aluminum were tested using the following tests:

I—610 tape adhesion

II—gloss at 60 deg.

III—Hoffman Scratch (gms to break surface)

IV—S-42 Tabor at 500 g

V—Glass transition temp (Tg)

VI—Pasteurization test comprising submersion of coated aluminum can body stock at 12 micron thickness, curing and baking for 3 min at 400 F., then submerging in a water solution of 1.0% dish detergent at 180 F., followed by test I.

ZDA Test Compositions

The following table lists the composition of each formulation tested. Samples 1 and 6 are the "controls". They are either Epoxy Acrylate or Urethane Acrylate based and do not contain either the solid or the liquid ZDA. Sample numbers 2 through 5 and 7 through 10 contain the solid ZDA, while samples numbers 11 through 18 employ the soluble ZDA.

| | Components | | | | | | | |
|---|---|---|---|---|---|---|---|---|
| Sample number | Epoxy Diacrylate Oligomer | Urethane Acrylate Oligomer | Solid Metallic Zinc Diacrylate | Zinc Phthalate Diester in 50% 1,3 Butylene Glycol Diacrylate | 1,3 Butylene Glycol Diacrylate | Dipropylene Glycol Diacrylate | 3 mole Ethoxylated Tri-methylolpropane Tri-acrylate | Alpha Hydroxy Ketone Photo-initiator |
| 1 | 55.4 | X | 0 | 0 | 15.7 | 15.7 | 9.2 | 4.0 |
| 2 | 51.3 | X | 5.6 | 0 | 17.0 | 13.9 | 8.2 | 4.0 |
| 3 | 47.1 | X | 11.0 | 0 | 18.5 | 12.2 | 7.2 | 4.0 |
| 4 | 42.4 | X | 16.5 | 0 | 20.0 | 10.7 | 6.4 | 4.0 |
| 5 | 37.8 | X | 22.0 | 0 | 21.6 | 9.2 | 5.4 | 4.0 |
| 6 | X | 61.1 | 0 | 0 | 12.9 | 12.9 | 9.1 | 4.0 |
| 7 | X | 55.9 | 5.6 | 0 | 11.6 | 11.6 | 8.2 | 4.0 |
| 8 | X | 52.1 | 10.8 | 0 | 10.0 | 10.0 | 7.0 | 4.0 |
| 9 | X | 47.7 | 16.0 | 0 | 8.6 | 8.6 | 6.1 | 4.0 |
| 10 | X | 42.5 | 21.3 | 0 | 7.4 | 7.4 | 5.4 | 4.0 |
| 11 | 51.3 | X | 0 | 11.4 | 11.4 | 13.9 | 8.2 | 4.0 |
| 12 | 47.3 | X | 0 | 22.0 | 7.5 | 12.2 | 7.2 | 4.0 |
| 13 | 42.4 | X | 0 | 33.0 | 3.5 | 10.7 | 6.4 | 4.0 |
| 14 | 37.8 | X | 0 | 44.0 | 0 | 9.2 | 5.4 | 4.0 |
| 15 | X | 55.9 | 0 | 11.2 | 9.1 | 11.6 | 8.2 | 4.0 |

-continued

| Sample number | Epoxy Diacrylate Oligomer | Urethane Acrylate Oligomer | Solid Metallic Zinc Diacrylate | Zinc Phthalate Diester in 50% 1,3 Butylene Glycol Diacrylate | 1,3 Butylene Glycol Diacrylate | Dipropylene Glycol Diacrylate | 3 mole Ethoxylated Trimethylolpropane Triacrylate | Alpha Hydroxy Ketone Photoinitiator |
|---|---|---|---|---|---|---|---|---|
| 16 | X | | 52.1 | 21.6 | 5.3 | 10 | 7.0 | 4.0 |
| 17 | X | | 47.7 | 32.0 | 1.6 | 8.6 | 6.1 | 4.0 |
| 18 | X | | 41.7 | 41.8 | 0 | 7.3 | 5.3 | 4.0 |

Surprisingly, the panels coated with compositions according to the invention passed each of tests whereas the corresponding formulations using C rather than D failed test IX, and resulted in poorer results in each of tests I through VIII.

A) 610 Cross Hatch Tape Adhesion Test

Adhesion tests were performed on formulations using the solid ZDA and compared to those containing soluble Zinc HEA Phthalate Diester in 50% 1,3 Butylene Glycol Diacrylate(1,3 BGDA). The adhesion results depicted in the following graph are for formulations based on an Epoxy Diacrylate oligomer and represent formulation numbers 1 through 5 and 11 through 14 listed in the previous table. Sample number 1 contains no ZDA while samples 2 through 5 employ the solid ZDA and sample numbers use the solid ZDA. Concentrations of this material range from a low 5.6% to a high of 22.0%.

When no ZDA is added the adhesion is very poor, exhibiting 95% adhesion loss. As the solid ZDA level increases the adhesion gradually improves showing a 50% adhesion loss at a 5.6% level of ZDA to only a 5% adhesion loss at a 22% concentration. In contrast complete adhesion is realized with the soluble ZDA at the lowest the lowest concentration of 5.6%.

Gardner Gloss at a 60 Degree Angle

Solid ZDA is often added to coatings to enhance their adhesion to a wide variety of substrates. As the data outlined in the previous section indicate a 20–25% level of addition is required to obtain the desired adhesion result. Since standard ZDA is a solid fine white powder that must be dispersed into the base formulation, the unwanted effect of significantly reducing the gloss of the coated and cured formulation may occur.

The following table shows the effect that of addition solid ZDA has on gloss and is compared to the gloss attained when the soluble ZDA is used at the same level. These tests were conducted on both epoxy acrylate and urethane acrylate based oligomer formulations. As the gloss data indicates when the level of solid ZDA increases the gloss of the cured film is diminished. In contrast, the gloss of the coatings containing the soluble ZDA remains unchanged.

Gloss as a Function of Level and Type of ZDA Employed

| Sample # | Base Oligomer Type | Concentration of Solid ZDA | Concentration of Soluble ZDA | Gloss at 60 Degrees |
|---|---|---|---|---|
| 1 | Epoxy Acrylate | "Control" No ZDA | NA = Not Added | 109.2 |
| 2 | Epoxy Acrylate | 5.6% | NA | 102.2 |
| 3 | Epoxy Acrylate | 11.0% | NA | 90.7 |
| 4 | Epoxy Acrylate | 16.5% | NA | 83.6 |
| 5 | Epoxy Acrylate | 22.0% | NA | 77.3 |
| 6 | Urethane Acrylate | "Control" No ZDA | NA | 90.6 |
| 7 | Urethane Acrylate | 5.6% | NA | 83.2 |
| 8 | Urethane Acrylate | 10.8% | NA | 77.6 |
| 9 | Urethane Acrylate | 16.0% | NA | 71.4 |
| 10 | Urethane Acrylate | 21.3% | NA | 70.6 |
| 11 | Epoxy Acrylate | NA | 5.7% | 99.4 |
| 12 | Epoxy Acrylate | NA | 11.0% | 98.9 |
| 13 | Epoxy Acrylate | NA | 16.5% | 96.4 |
| 14 | Epoxy Acrylate | NA | 22.0% | 94.5 |
| 15 | Urethane Acrylate | NA | 5.7% | 95.2 |
| 16 | Urethane Acrylate | NA | 10.8% | 95.4 |
| 17 | Urethane Acrylate | NA | 16.0% | 94.5 |
| 18 | Urethane Acrylate | NA | 20.9% | 95.3 |

C) HOFFMAN SCRATCH RESISTANCE

The Hoffman Scratch test employs a device that measures the force required in grams to scratch or abrade the surface of a film or coating. The higher the force the harder and more resilient the film.

A series of formulations based on an Epoxy Diacrylate oligomer were tested using this method. They are represented by formulation numbers 1 through 5 and 11 through 14 listed in the ZDA Test Composition. Formulation 1 is the "Control" material and contains no ZDA. Formulations 2 through 5 employ the solid ZDA, while Formulations 11 through 14 contain the soluble ZDA at corresponding levels. The following lists the level and type of ZDA used and the Hoffman Scratch values attained.

Hoffman Scratch Results

| FORMULATION NUMBER | ZDA LEVEL AND TYPE | HOFFMAN SCRATCH RESISTANCE IN GRAMS |
|---|---|---|
| 1 | "Control" No ZDA added | 50 |
| 2 | 5.6% Solid ZDA | 25 |
| 3 | 11.0% Solid ZDA | 25 |

-continued

| FORMULATION NUMBER | ZDA LEVEL AND TYPE | HOFFMAN SCRATCH RESISTANCE IN GRAMS |
| --- | --- | --- |
| 4 | 16.5% Solid ZDA | 25 |
| 5 | 22.0% Solid ZDA | 25 |
| 11 | 5.6% Soluble ZDA | 1200 |
| 12 | 11.0% Soluble ZDA | 1100 |
| 13 | 16.5% Soluble ZDA | 1000 |
| 14 | 22.0% Soluble ZDA | 1000 |

Solid ZDA=The standard product
Soluble ZDA=Zinc HEA Phthalate Diester in 50% 1,3 BGDA As the results indicate the formulations containing the solid or standard ZDA are much softer and less scratch resistant than those containing the soluble ZDA. The abrasion resistance in each case does not improve with higher levels of ZDA.

D) S-42 TABER CYCLES TO WEAR THROUGH

Another measure of a coating or a film's hardness properties can be characterized by the "S42 Taber Test". This involves attaching a strip of sandpaper (S-42 type) to a rubber wheel, placing the wheel in contact with the coating to be tested, applying a 500 gram weight and counting the number of revolutions or cycles required to wear through 25 microns of the coating applied to a substrate.

All of the formulations listed in the "ZDA Test Composition" section were evaluated using this technique. The following table provides a listing of the base composition, the level and type of ZDA used as well as the S-42 Taber results.

S-42 TABER RESULTS

| Formulation Number | Base Oligomer Employed, EA = Epoxy Acrylate, UA = Urethane Acrylate | Level and Type of ZDA Used, Solid = Std. Prod. Soluble = Zinc HEA Phthalate Diester in 50% 1,3 BGDA | S-42 Cycles to Wear Through a 25 Micron Film Thickness |
| --- | --- | --- | --- |
| 1 | EA | "Control" No ZDA Added | 92 |
| 2 | EA | 5.6% Solid | 102 |
| 3 | EA | 11.0% Solid | 108 |
| 4 | EA | 16.5% Solid | 120 |
| 5 | EA | 22.0% Solid | 144 |
| 6 | UA | "Control" No ZDA Added | 114 |
| 7 | UA | 5.6% Solid | 120 |
| 8 | UA | 11.0% Solid | 130 |
| 9 | UA | 16.5% Solid | 130 |
| 10 | UA | 22.0% Solid | 135 |
| 11 | EA | 5.6% Soluble | 132 |
| 12 | EA | 11.0% Soluble | 168 |
| 13 | EA | 16.5% Soluble | 168 |
| 14 | EA | 22.0% Soluble | 168 |
| 15 | UA | 5.6% Soluble | 132 |
| 16 | UA | 11.0% Soluble | 150 |
| 17 | UA | 16.5% Soluble | 150 |
| 18 | UA | 22.0% Soluble | 162 |

As the results indicate, as the ZDA content increases so do the number of cycles required to wear through the coating. However, the average number of cycles to wear through is approximately 35% higher in the Epoxy Acrylate formulations and 15% higher in the Urethane Acrylate systems when the soluble ZDA is used instead of the standard solid ZDA.

E) GLASS TRANSITION TEMPERATURE AS A FUNCTION OF SOLUBLE ZDA ADDITION

The Tg value is another measure of the hardness and/or resiliency of a cured film or coating. A Differential Scanning Calorimeter (DSC) was used to measure the Tg of a series of coatings based on an acrylated urethane oligomer. The "control" formulation contained no soluble ZDA, while the subsequent compositions contained soluble ZDA ranging in concentration from a low of 5.6% up to 20.9%.

The following table relates the effect on Tg as a function of the soluble Zinc Salt level.

| Formulation # | Weight % Zinc Phthalate Diester in 50% 1,3 BGDA | Glass Transition Temperature, Degrees Centigrade |
| --- | --- | --- |
| 6 | 0.0 | 68.81 |
| 15 | 5.6 | 71.13 |
| 16 | 10.8 | 78.7 |
| 17 | 16.0 | 85.9 |
| 18 | 20.9 | 96.5 |

As the results indicate as the soluble zinc salt concentration the Tg also increases again demonstrating the effectiveness of the soluble ZDA on hardness properties.

F) RADIATION CURABLE COATINGS FOR THE EXTERIOR OF METAL 2-PIECE AND 3-PIECE FOOD AND BEVERAGE CONTAINERS

This application is very difficult for radiation curable technology as the coating must withstand the rigorous process conditions associated with the pasteurization and retort of the food or beverage within the can. In addition, the substrate used to manufacture the can body is very difficult to adhere to. In the case of 2-piece cans this is usually aluminum, whereas 3-piece cans are made from tin plated steel or tin free steel.

At this point, the use of radiation curable coatings for this application is limited to containers that do not go through the pasteurization or retort process. This represents only a very small portion of the vast can market.

There are two different methods of initiation of a coating using high intensity ultra violet light. One employs a C=C acrylate double reaction using a photoinitiator to produce free radicals. The other relies on a cationic reaction that produces an acid catalyst upon absorption of high intensity light. This acid initiates a ring opening reaction of the epoxide groups causing polymerization.

Variations of each of these types of chemistry were tried separately and in combination for this application without success until the soluble ZDA was used in combination with a cationic based chemistry and a free radical initiator.

The following table lists the successful formulation for each process.

Formulation that Passes the Pasteurization Process

| COMPONENT | CHEMICAL DESCRIPTION | WEIGHT % |
| --- | --- | --- |
| Sarcat K-126 | Cycloaliphatic Diepoxide | 63.68 |
| TP440 | Trifunctional Polyol | 7.07 |
| CD1011 | Triayl Sulfonium Hexafluoroatimonate in 50% Propylene Carbonate | 4.24 |
| NTX4225B | Zinc HEA Phthalate Diester in 50% TPGDA | 23.75 |
| KIP-150 | Polymeric Alpha Hydroxy Ketone Free Radical PI | 1.25 |
| TOTAL | | 100.0 |

Formulation that Passes the Retort Process

| COMPONENT | CHEMICAL DESCRIPTION | WEIGHT % |
|---|---|---|
| Sarcat K-126 | Cycloaliphatic Diepoxide | 60.47 |
| TP440 | Trifunctional Polyol | 11.75 |
| CD1011 | Triayl Sulfonium Hexafluoroatimonate in 50% Propylene Carbonate | 4.04 |
| NTX 4238 | Zinc CN130 Succinate Diester | 22.55 |
| KIP-100F | Alpha Hydroxy Ketone Free Radical PI | 1.19 |
| TOTAL | | 100.0 |

The following details the coating and curing process employed for each composition along with the Pasteurization and Retort conditions utilized. A description of the substrate used for each test is also provided.

Test Substrates:
  Pasteurization: Aluminum "ANC" stock
  Retort: Tin plated and tin free panels
Coating Conditions:
  Each coating was applied to the appropriate substrate using a zero that yields a nominal film thickness of 5–7 microns.
Curing Conditions:
  Upon application to the substrate each coating was cured at a conveyor speed of 50 fpm using one 300 w/in., Hg lamp. The integrated dose was 265 mj/sq.cm., as measured using an International Light, model I390 radiometer. After UV curing each panel was baked for 3 minutes at 200° C. .
Pasteurization Conditions:
  The aluminum 'ANC" panels were submerged in a 1.0% solution of Joy dish soap for 10 minutes at 82° C. The panels were then rinsed with cool tap water, dabbed dry, and crosshatch adhesion testing was performed using 610 tape. No adhesion loss was detected.
Retort Conditions:
  After curing the tin-plated and the tin free panels were bent 180 degrees. If the coating passed the 180 degree bend test the panels were then exposed to the Retort process. The Retort conditions were 30 minutes at 200° C. and 15 psi. Under these conditions no adhesion loss of the coating was observed along the radius of the bend.

Example 10

Peroxide Curable PVC Plasitsol Adhesive Compositions for Automotive Sealant Applications Comparative compositions comprising 5 parts per hundred of a 50/50 blend of zinc diacrylate and zinc dimethacrylate adhesion promoters for metal in a PVC resin/plasticizer/filler/trimethylolpropane trimethacrylate/peroxide automotive sealant base compound were prepared and measured for lap shear adhesion versus compositions of the invention wherein 5 parts per hundred of a compound according to Example 1 was used in place of the 50/50 blend of zinc diacrylate and zinc dimethacrylate.

The adhesive composition of the invention resulted in cohesive failure whereas the comparative composition of the prior art resulted in adhesive failure, which is undesirable for automotive applications. Furthermore, the preparation of the adhesive compositions was easier with the compound of the invention because the comparative adhesion promoters were difficult to incorporate due to the fact that they are in powder form, reduce viscosity significantly such that a thixotrope is needed to prevent sag, and requires additional heating of the base compound to disperse the comparative adhesion promoters, which can result in some premature curing. The compounds of the invention are provided as a liquid, increase or maintain compound viscosity, and result in shorter mixing times.

Example 11

Peroxide Curable Unsaturated Polyester Laminating Resins

Heat resistance of unsaturated polyester based laminating or binder formulations can be improved by incorporation of metal salts. However, the metal salts of the prior art are very difficult to disperse in unfilled systems, and result in extended gel times and reduced viscosity. Such a formulation comprising unsaturated polyester resin, styrene monomer, and peroxide was prepared, and attempts were made to incorporate zinc diacrylate (comparative) or a compound according to Example 1.

The compounds of the invention were much easier to disperse, and maintained acceptable gel time and viscosity without reformulation, whereas the comparative metal compound increased gel time and reduced viscosity significantly.

While the invention has been described in detail herein, various modifications, alternatives, and improvements should become apparent to those skilled in this art without departing from the spirit and scope of the invention as set forth in the appended claims.

What is claimed is:

1. A radiation curable coating, adhesive, or photoresist ink composition comprising (A) at least one oil soluble polymerizable, ethylenically unsaturated compound of formula

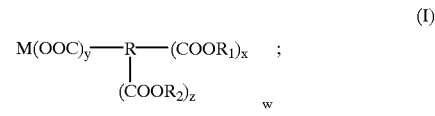

(I)

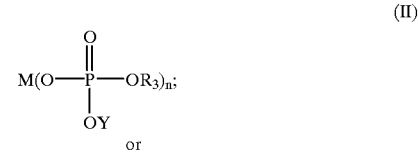

(II)

or

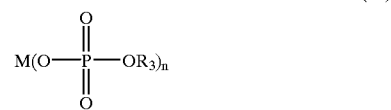

(III)

wherein
  M is one or more metal atoms of valence n, wherein n=y w, wherein M is optionally more than one metal atom, with the proviso that the global equivalent metal valence is n=w y; n is an integer of about 1–6;
  R is a residue of a compound having anhydride and/or carboxylic acid groups with an initial equivalent carboxy equivalent functionality defined by the equation f=x+y+z, wherein f is an integer of about 2 to 30;
  $R_1$ is a residue of a hydroxy-containing ethylenically unsaturated compound;

R₂ is hydrogen or a residue of a hydroxy-containing ethylenically unsaturated compound different from R₁ or another metal group M;

R₃ is a residue of a hydroxy-containing ethylenically unsaturated compound;

w is a number of moieties having residue R required for metal valence n;

x is an integer of about 1 f–1;

y is an integer of about 1 to 2;

z is an integer of about 0 to f–2;

Y is hydrogen or R₃;

(B) at least one copolymerizable ethylenically unsaturated monomer or oligomer; and (C) at least one unimolecular or bimolecular photoinitiator; said composition being substantially free of peroxide initiator.

2. The composition according to claim 1 wherein radiation is either provided by a source, of ultraviolet light or by electron beam.

3. The composition according to claim 1 wherein M is selected from the group consisting of lithium, sodium, potassium, cesium, magnesium, calcium, strontium, barium, titanium, zirconium, vanadium, chromium, molybdenum, tungsten, manganese, iron, cobalt, nickel, palladium, copper, zinc, cadmium, mercury, boron, aluminum, gallium, indium, silicon, germanium, tin, lead, antimony and bismuth.

4. The composition according to claim 1 wherein compound (A) is said formula (I) and R is a residue of an ethylenically unsaturated compound having anhydride and/or carboxylic acid groups.

5. The composition according claim 4 wherein R is a residue of a compound selected from the group consisting of phthalic anhydride, isophthalic acid, terephthalic acid, tetrabromophthalic anhydride, tetrahydrophthalic anhydride, hexahydrophthalic anhydride, itaconic anhydride, itaconic acid, phthalic acid, trimellitic anhydride, pyromellitic anhydride, 5-norbornene-endo-2,3-dicarboxylic anhydride, naphthyl anhydride, naphthalene tetracarboxylic acid dianhydride, maleic anhydride, succinic anhydride, chlorendic anhydride, maleic acid, succinic acid, fumaric acid, oxalic acid, malonic acid, glutaric acid, adipic acid, dimer fatty acids, and styrene/maleic anhydride polymers.

6. The composition according to claim 1 wherein R₁ or R₃ is a residue of a compound which contains an ethylenically unsaturated group selected from the group consisting of (meth)acrylic, allyl, propenyl, and vinyl.

7. The composition according to claim 6 wherein said R₁ or R₃ is a residue of a compound selected from the group consisting of hydroxyethyl (meth)acrylate, hydroxypropyl (meth)acrylate, hydroxybutyl (meth)acrylate, (C₁ to C₆) alkyl glycidyl (meth)acrylates, aryl glycidyl (meth) acrylates, allyl glycidyl (meth)acrylate, trimethylolpropane mono- and di-(meth)acrylate, pentaerythritol mono-, di-, and tri-(meth)acrylate, dipentaerythritol mono-, di-, tri-, tetra-, and penta-(meth)acrylate, glycerol mono- and di-(meth) acrylate, neopentyl glycol mono(meth)acrylate, hexanediol mono(meth)acrylate, tris(2-hydroxyethyl) isocyanurate mono- and di-(meth)acrylate, ethoxylated or propoxylated versions of all of the above, polyethylene glycol mono (meth)acrylate, polypropylene glycol mono(meth)acrylate, polyethylene/propylene glycol mono(meth)acrylate, polybutylene glycol mono(meth)acrylate, polytetramethylene glycol mono(meth)acrylate, and hydroxy polycaprolactone mono(meth)acrylate.

8. The composition according to claim 1 wherein said composition is in the form of a solution.

9. The composition according to claim 8 wherein said composition further comprises an inert solvent.

10. A process of preparing solution of claim 8 comprising forming said compound (A) in the presence of said copolymerizable ethylenically unsaturated monomer or oligomer (B) and optionally in the presence of an inert solvent.

11. The composition according to claim 8 substantially free of organic insoluble metal salt.

12. The composition according to claim 1 wherein said copolymerizable ethylenically unsaturated monomer or oligomer (B) is selected from the group consisting of (meth) acrylic monomer, (meth)acrylic oligomer, vinyl monomer, vinyl oligomer, allyl monomer, allyl oligomer, propenyl monomer, propenyl oligomer, glycol ether, glycidyl ether, glycidyl ester, and mixtures thereof.

13. A polymeric composition prepared by curing a composition according to claim 1 with radiation.

14. The composition of claim 13 in the form of a coating, adhesive, ink, photoresist, or molded article.

15. A process of preparing polymerizable, ethylenically unsaturated compound (A) of formula

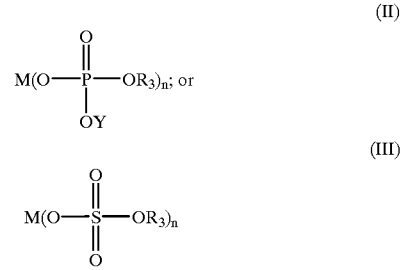

wherein

M is one or more metal atoms of valence n, wherein n=y·w, wherein M is optionally more than one metal atom, with the proviso that the global equivalent metal valence is n=w·y;

n is an integer of about 1–6;

R is a residue of a compound having anhydride and/or carboxylic acid groups with an initial equivalent carboxy equivalent functionality defined by the equation f=x+y+z, wherein f is an integer of about 2 to 30;

R₁ is a residue of a hydroxy-containing ethylenically unsaturated compound;

R₂ is hydrogen or a residue of a hydroxy-containing ethylenically unsaturated compound different from R₁ or another metal group M;

R₃ is a residue of a hydroxy-containing ethylenically unsaturated compound;

w is a number of moieties having residue R required for metal valence n;

x is an integer of about 1 to f–1;

y is an integer of about 1 to 2;

z is an integer of about 0 to f–2; and

Y is hydrogen or R₃;

comprising reacting a hydroxy compound with sulfur oxide, or phosphorus oxide compound to form an acid functional compound, and reacting said acid functional compound with a metal compound.

16. The process according to claim 15 wherein said metal compound is selected from the group consisting of metal oxide, halide, alkoxide, hydroxide, nitrate, sulfate, carboxylate, and carbonate.

17. A process of preparing a coating, adhesive, ink, or molded article comprising reacting in the presence of radiation a peroxide-free solution comprising (A) at least one compound according to formula $$M(OOC)_y\text{—}R\text{—}(COOR_1)_x \quad ; \quad (I)$$
$$\underset{(COOR_2)_z}{|} \quad _w$$

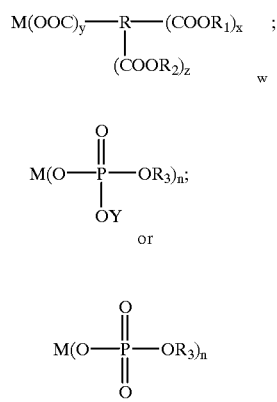

wherein

M is one or more metal atoms of valence n, wherein n=y·w, wherein M is optionally more than one metal atom, with the proviso that the global equivalent metal valence is n=w·y;

n is an integer of about 1–6;

R is a residue of a compound having anhydride and/or carboxylic acid groups with an initial equivalent carboxy equivalent functionality defined by the equation f=x+y+z, wherein f is an integer of about 2 to 30;

$R_1$ is a residue of a hydroxy-containing ethylenically unsaturated compound;

$R_2$ is hydrogen or a residue of a hydroxy-containing ethylenically unsaturated compound different from $R_1$ or another metal group M;

$R_3$ is a residue of a hydroxy-containing ethylenically unsaturated compound;

w is a number of moieties having residue R required for metal valence n;

x is an integer of about 1 to f–1;

y is an integer of about 1 to 2, z is an integer of about 0 to f–2; and

Y is hydrogen or $R_3$; and (B) at least one copolymerizable ethylenically unsaturated monomer or oligomer.

18. A molded article prepared by the process of claim 17 having a refractive index useful for lenses.

19. The molded article according to claim 18 having a refractive index between about 1.50 and 1.60.

20. The molded article according to claim 18 having a transparency substantially equivalent to that of glass.

21. The molded article according to claim 18 wherein said ethylenically unsaturated monomer comprises diallyl glycol carbonate.

22. A clear, transparent molded article comprised of a radiation cured thermoset copolymer of a monomer mixture comprising (A) a compound according to formula

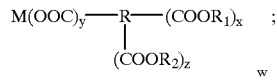

-continued

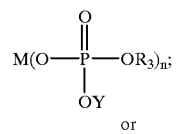

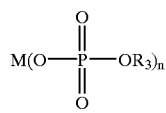

wherein

M is one or more metal atoms of valence n, wherein n=y–w, wherein M is optionally more than one metal atom, with the proviso that the global equivalent metal valence is n=w–y;

n is an integer of about 1–6;

R is a residue of a compound having anhydride and/or caboxylic acid groups with an initial equivalent carboxy equivalent functionality defined by the equation f=x+y+z, wherein f is an integer of about 2 to 30;

$R_1$ is a residue of a hydroxy-containing ethylenically unsaturated compound;

$R_2$ is hydrogen or a residue of a hydroxy-containing ethylenicalty unsaturated compound different from $R_1$ or another metal group M;

$R_3$ is a residue of a hydroxy-containing ethylenically unsaturated compound;

w is a number of moieties having residues R required for metal valence n;

x is an integer of about 1 to f–1;

y is an integer of about 1 to 2;

z is an integer of about 0 to f–2;

Y is hydrogen or $R_3$; and at least one laminating resin.

(B) a polyfunctional (meth)acrylate or allylic compound.

23. The article according to claim 1 further including a monomer selected from the group consisting of (meth) acrylates, styrene, vinyl ethers, epoxys, and propenyl ethers.

24. A radiation curable composition suitable for laminating resins having high heat distortion temperature, comprising at least one oil soluble compound selected from the group consisting of the formulae

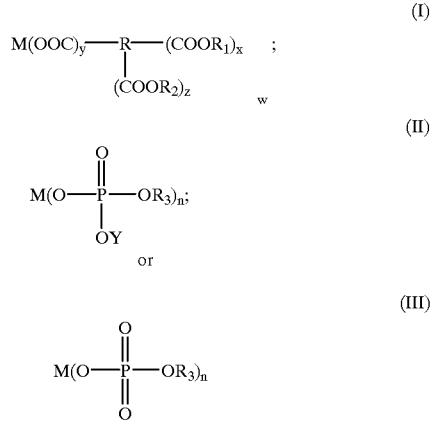

and mixtures thereof, wherein

M is one or more metal atoms of valence n, wherein n=y–w, wherein M is optionally more than one metal atom, with the proviso that the global equivalent metal valence is n=w−y; n is an integer of about 1–6;

R is a residue of a compound having anhydride and/or carboxylic acid groups with an initial equivalent carboxy equivalent functionality defined by the equation f=x+y+z, wherein f is an integer of about 2 to 30;

$R_1$ is a residue of a hydroxy-containing ethylenically unsaturated compound;

$R_2$ is hydrogen or a residue of a hydroxy-containing ethylenically unsaturated compound different from $R_1$ or another metal group M;

$R_3$ is a residue of a hydroxy-containing ethylenically unsaturated compound;

w is a number of moieties having residue required for metal valence n;

x is an integer of about 1 to f−1;

y is an integer of about 1 to 2;

z is an integer of about 0 to f−2;

Y is hydrogen or $R_3$; and at least one laminating resin.

25. The composition according to claim 1 wherein said copolymerizable monomer or oligomer is selected from the group consisting of (meth)acrylates, styrene, vinyl ethers, epoxys, and propenyl ethers.

26. A coating, adhesive, ink, molded article or photoresist prepared by exposing a composition according to claim 25 to sufficient radiation to polymerize and crosslink said composition.

27. The composition according to claim 25 wherein said copolymerizable monomer or oligomer is selected from the group consisting of epoxys, vinyl ethers, and propenyl ethers, and said composition further includes a cationic photoinitiator, said composition being suitable for hybrid curing under the influence of radiation.

28. The composition according to claim 27 wherein said cationic photoinitiator is selected from the group consisting of diaryl iodonium salts and triaryl sulfonium salts.

29. The composition according to claim 28 wherein said cationic photoinitiator is selected from the group consisting of diaryliodonium hexafluoroantimonate, triarylsulfonium hexafluoroantimonate, triarylsulfonium hexafluorophosphate, and cyclopentadiene hexafluorophosphate.

30. The composition according to claim 27 further including a free radical photoinitiator and a monomer selected from the group consisting of (meth)acrylates, styrene, vinyl compounds, and N-vinyl compounds.

31. The composition according to claim 30 wherein said free radical photoinitiator is unimolecular or bimolecular.

32. The composition according to claim 1 wherein said photoinitiator is a bimolecular photoinitiator selected from the group consisting of benzophenone, and derivatives of benzophenone, and is used in combination with a hydrogen donating source.

33. A process comprising coating a metal substrate with a composition according to claim 26, thereby forming a coating, and curing said coating by exposing said coating to radiation.

34. The process according to claim 33 further comprising exposing said coating to heat.

35. A coated metal article prepared by a process according to claim 34, which can withstanding pasteurization and retort conditions substantially without degradation of said coating.

36. The composition according to claim 27 suitable for ultraviolet radiation curable powder coatings, inks, and adhesives, said composition being solid at room temperature.

37. A process of coating a substrate comprising applying the solid powder coating composition of claim 36 to said substrate and curing said powder coating composition with radiation and heat.

* * * * *